United States Patent

Yamaguchi

Patent Number: 5,294,634
Date of Patent: Mar. 15, 1994

[54] OSTEOGENESIS PROMOTER

[75] Inventor: Masayoshi Yamaguchi, Shizuoka, Japan

[73] Assignees: Zeria Pharmaceutical Co., Ltd., Tokyo; Hamari Chemicals Co., Ltd., Osaka, both of Japan

[21] Appl. No.: 842,174

[22] PCT Filed: Sep. 28, 1990

[86] PCT No.: PCT/JP90/01255

§ 371 Date: Apr. 2, 1992

§ 102(e) Date: Apr. 2, 1992

[87] PCT Pub. No.: WO91/04737

PCT Pub. Date: Apr. 18, 1991

[30] Foreign Application Priority Data

Oct. 2, 1989 [JP] Japan ................... 1-255325

[51] Int. Cl.$^5$ ............... A61K 31/415; C07F 3/06
[52] U.S. Cl. ................... 514/400; 548/101
[58] Field of Search ........................... 548/101

[56] References Cited

FOREIGN PATENT DOCUMENTS 63-229058 9/1988 Japan .

OTHER PUBLICATIONS

CA 115(4):35753t Carnosine as an osteogenesis promoter. Yamaguchi, p. 417, 1991.
CA 117(5):40150g The gastric mucosal...ulcer. Masao et al., p. 62, 1992.
Research in Experimental Medicine, vol. 190, Apr. 1990, pp. 105–110, Springer–Verlag; M. Yamaguchi et al.: "A new zinc compound, Beta-alanyl-L-histidinato zinc, stimulates bone growth in weanling rats".
Pharmacology, vol. 41, Dec. 1990, pp. 345–349, S. Karger AG, Basel, CH; M. Yamaguchi et al.: "Effect of the new zinc compound Beta-alanyl-L-histidinato zinc on bone metabolism in elderly rats".
Journal of the American Podiatry Association, vol. 66, No. 8, Aug. 1976, pp. 604–617; F. Kase et al.: "A literature search for the methods and materials used to stimulate ostegenesis".
Research in Experimental Medicine, vol. 186, 1986, pp. 337–342 Springer-Verlag; M. Yamaguchi et al.: "Effect of essential trace metals on bone metabolism in weanling rats: Comparison with zinc and other metals' actions".
Patent Abstracts of Japan, vol. 14, No. 522 (C-778) [4465], Nov. 15th, 1990; & JP-A-2 221 230 (Kinuko Nagai) Apr. 9, 1990.
Chemical Abstracts (CA) 95 (17): 144088u Oct. 26, 1981, Lee et al.

*Primary Examiner*—Mary C. Lee
*Assistant Examiner*—Joseph K. McKane
*Attorney, Agent, or Firm*—Oblon, Spivak, McClelland, Maier & Neustadt

[57] ABSTRACT

The present invention relates to an orally-administrable osteogenesis promoter, which comprises, as an active ingredient, a zinc salt or complex of L-carnosine, has excellent osteogenesis-accelerating action, and is extremely low in toxicity and side effects.

8 Claims, No Drawings

OSTEOGENESIS PROMOTER

TECHNICAL FIELD

This invention relates to an osteogenesis promoter (osteogenic activator) which comprises, as an active ingredient, a zinc salt or complex of L-carnosine.

BACKGROUND ART

With advancing age, the bone mass decreases. In the younger generation, calcium in bones may also be congenitally or idiopathically abnormally absorbed in blood, so that calcium in bones is reduced and the bone mass is hence lowered, resulting in imperfect bone metabolism and osteogenesis.

Disordered bone metabolism and osteogenesis will bring about fracture, osteomalacia, osteoporosis and/or low back pain. In recent years, the aged people are rapidly increasing in the world and osteogenesis imperfecta increases correspondingly. Also, similar diseases are increasing in the younger generation due to calcium deficiency caused by the disproportionately eating habit.

Experimental markers for osteogenesis and calcification include measurements or determinations of calcium content, alkaline phosphatase activity and DNA content in bones. It is said that the formation and metabolism of bones are more active as these contents or levels in the bone increase.

Calcitonin and active vitamin $D_3$ drugs have heretofore been used generally in medicinal therapy of diseases caused by imperfect osteogenesis. Besides, hormone drugs and calcium preparations are also used.

Although the calcitonin shows an excellent effect on pains in osteoporosis, it does not exhibit any effects when orally administrated because it is a peptide. Its only use as an injection is however accompanied by problems of inconvenient administration and pain upon its administration. On the other hand, the active vitamin $D_3$ drugs are insufficient in effects such as bone-forming action and pain-alleviating action and involve such problems as bring about hypercalcemia.

Further, it has been shown in vivo [Metabolism, 35, 1044–1047 (1986); and Biochem. Pharmacol., 35, 773–777 (1986)] and in vitro [Biochem. Pharmacol., 36, 4007–4012 (1987); and ibid., 37, 4075–4080 (1988)] that zinc plays an important role as an activator for stimulation and calcification in osteogenesis. Furthermore, it has been shown that zinc stimulates bone protein synthesis [Biochem. Parmacol., 37, 4075–4080 (1988)].

However, pharmaceutical use of zinc has not been attained though it has been suggested that it has osteogenesis-accelerating action. Zinc itself involves a problem in points of absorption, metabolism and toxicity. There has thus been a demand for the development of a substance excellent in bone-forming property.

On the other hand, an L-carnosine zinc salt is a zinc salt of L-carnosine derived from beta-alanine and L-histidine. The salt has been known to have peptic ulcer-healing action (Japanese Patent Application Laid-Open No. 33270/1984) and preventing and healing action of hepatopathy (Japanese Patent Application Laid-Open No. 14728/1988). It has been suggested that inhibition of free-radical reaction (anti-active-oxygen action) participates in mechanism of anti-ulcer action [Journal of Japanese Digestive Disease Society, 85. Extra edition, 644 (1987)]. It has however been not known that the zinc salt or complex of L-carnosine has osteogenesis-accelerating action.

With the foregoing circumstances in view, the present inventors have carried out an extensive investigation. As a result, it has been found that the zinc salt or complex of L-carnosine has excellent osteogenesis-accelerating action, and an osteogenesis-accelerating agent comprising, as an active ingredient, this compound is extremely low in toxicity and side effects and useful in treating fracture, osteomalacia and the like, which are caused by a disorder of bone metabolism or osteogenesis, leading to completion of the present invention.

DISCLOSURE OF INVENTION

The present invention is directed to a new type of osteogenesis promoter which comprises, as an active ingredient, a zinc salt or complex of L-carnosine and is quite different from the conventional calcitonin and active vitamin $D_3$ drugs.

The zinc salt or complex of L-carnosine may be present in two types of amorphous and crystalline forms. There is no difference in their osteogenesis-accelerating actions. By the way, the determination which of the amorphous and crystalline forms the zinc salt or complex of L-carnosine has can be done, for example, by observation through an electron microscope, infrared absorption spectrum and X-ray diffraction pattern.

The zinc salt or complex of L-carnosine is prepared, for example, by reacting a zinc salt and an alkali metal compound with L-carnosine in water or an organic solvent.

The crystalline zinc salt or complex of L-carnosine is obtained by using a zinc salt and an alkali metal compound in proportions of 0.8–1.2 moles and 1.6–2.4 moles, respectively, per mole of L-carnosine and reacting them with each other in a water-free or water-containing polar organic solvent either at room temperature or under heating (Japanese Patent Application Laid-Open No. 42471/1989). As examples of the polar organic solvent, may be mentioned alcohols such as methanol, ethanol and propanol, acetonitrile, dimethyl sulfoxide, N,N-dimethyl formaldehyde, tetrahydrofuran, acetone, and the like. Those containing water up to about 50% may be used. As the zinc salt, may be used both salts of inorganic acids and organic acids. As examples of the former zinc salts, may be mentioned zinc halides, zinc sulfate, zinc nitrate, zinc perchlorate, etc. As examples of the latter zinc salts, may be mentioned zinc salts of carboxylic acids such as zinc acetate, zinc acetylacetonate, etc. Any zinc salts may however be used so long as they advance the reaction. As the alkali metal compound, may be used lithium hydroxide, potassium hydroxide, sodium hydroxide, potassium alcoholate, sodium alcoholate, etc.

On the other hand, the amorphous zinc salt or complex of L-carnosine can be prepared by the same procedure as described above except that water is used in stead of the water-free or water-containing polar organic solvent.

The thus-obtained zinc salt or complex of L-carnosine may be added with pharmaceutically acceptable adjuvants to use it as a preparation for oral or parenteral administration. Particular preference is however given to oral administration. With respect to preparations for the oral administration, the above compound may be suitably combined with proper additives, for example, excipients such as lactose, mannitol, corn starch and crystalline cellulose; binders such as cellulose derivatives, gum arabic and gelatin; disintegrators such as calcium carboxymethyl cellulose; lubricants such as talc. and magnesium stearate; or the like, to form its tablets, powders, granules and capsules. In addition, these solid preparations may be formed into enteric preparations by using a coating base such as hydroxypropylmethyl cellulose phthalate, hydroxypropylmethyl cellulose acetate succinate, cellulose acetate phthalate or a methacrylate copolymer. Furthermore, the solid preparations may be formed into soft capsules by dissolving them in a medium-chain fatty acid triglyceride, safflower oil, soybean oil, polyethylene glycol 400 or the like. With respect to preparations for parenteral administration, the compound may be combined with, for example, water, ethanol, glycerol, conventionally-used surfactants and the like to form its injections. Alternatively, it may be formed into suppositories by using a base material for suppositories.

Their dose varies depending upon the age, weight and condition of a patient to be dosed, therapeutic effect, dosing method, and dosing period. In the case of the oral administration, the preparation is dosed one to three times a day in a range of 1–2000 mg/day, preferably 10–200 mg/day.

EXAMPLES

The present invention will hereinafter be described more specifically by Reference Example, Test Examples and Examples. However, these examples are not intended to limit this invention.

Reference Example

Preparation of a Crystalline Zinc Complex of L-Carnosine

In 100 ml of methanol was dissolved 3.51 g of sodium hydroxide, to which 9.96 g of L-carnosine was added to form a uniform solution. A solution with 9.67 g of zinc acetate dihydrate dissolved in 145 ml of methanol was added dropwise to the first-mentioned solution over 30 minutes under stirring. As a result, white precipitate occurred gradually. After completion of the dropping, the resulting mixture was stirred for 2 hours and then left to stand overnight. Thereafter, the mixture was filtered, and the resulting filter cake was washed with 140 ml of water and air-dried for 5 hours at 80° C., thereby obtaining 12.4 g of white powder in the form of crystals.

IR (KBr) cm$^{-1}$: 3292, 1626, 1563, 1389, 1262, 1230, 1117, 1060, 1030, 999, 982, 883, 787

| Elemental analysis (determined as $C_9H_{12}N_4O_3Zn$): | | | | |
|---|---|---|---|---|
| | C | H | N | Zn |
| Calculated (%) | 37.33 | 4.18 | 19.35 | 22.53 |
| Found (%) | 37.07 | 4.27 | 19.06 | 22.50 |

| X-ray diffraction pattern: | |
|---|---|
| Lattice spacing (d; angstrom) | Relative intensity (%; I/I$_0$) |
| 11.87 | 26 |
| 7.54 | 28 |
| 5.97 | 43 |
| 5.55 | 27 |
| 5.26 | 30 |
| 4.52 | 51 |
| 3.96 | 100 |
| 3.56 | 19 |
| 3.24 | 29 |
| 2.97 | 19 |
| 2.79 | 17 |
| 2.68 | 22 |
| 2.58 | 21 |
| 2.38 | 25 |
| 2.10 | 13 |
| 1.97 | 14 |
| 1.88 | 15 |
| 1.84 | 14 |
| 1.69 | 10 |
| 1.57 | 9 |
| 1.55 | 9 |
| 1.53 | 10 |

TEST EXAMPLE 1

Osteogenesis-Stimulating Action

The osteogenesis-stimulating action of the zinc complex of L-carnosine was confirmed by the calcium content, zinc content, alkaline phosphatase activity and DNA content in the femoral diaphysis of young rats used. Zinc sulfate was used as a comparative compound.

Materials and Method

Young Wistar rats were used regarding five rats as one group. Using, as an agent to be tested and a comparative compound, a solution, which had been obtained by dissolving the L-carnosine zinc complex in 1N hydrochloric acid and adjusting its pH to 7 with 1N sodium hydroxide, and a solution with zinc sulfate dissolved in distilled water, respectively, they were orally administered to respective groups. A control group was orally given with a solvent alone.

The agent to be tested was administered for 3 days once a day in an amount corresponding to 5.5 mg/kg body weight in terms of zinc. Upon elapsed time of 24 hours after the last dose, the rats were sacrificed and the femoral regions were taken out of each rat under light ether anesthesia. Soft tissues and bone marrow were removed from the femoral region. The diaphysis and epiphysis (including metaphyseal tissues) were separated from each other to form fragments of the femoral diaphysis.

Measurement of Calcium Content in Bone

The femoral diaphysis tissue was ashed for 24 hours at 640° C. to weigh the resulting ash. Thereafter, the ash was dissolved in 6N hydrochloric acid to measure its calcium content by atomic absorption spectrophotometry. The calcium content in the bone was expressed in terms of mg per g of the bone ash.

Determination of Alkaline Phosphatase Activity

The femoral diaphysis tissue was immersed into 3 ml of ice-cold 6.5 mM barbital buffer solution (pH: 7.4) and then cut into pieces to uniformly grind them by a Potter-Blvehjem homogenizer equipped with a Teflon pestle. The thus-ground tissue was disintegrated over 60 seconds by an ultrasonic disintegrator. The tissue thus disintegrated was centrifuged at 600×g for 5 minutes. The thus-obtained supernatant liquid was used for the determination of enzymatic activity. The alkaline phosphatase activity was determined in accordance with the Wallter-Schutt procedure [Bergmeyer HU (ed), Methods of enzymatic analysis, Vol. 1–2, Academic Press, New York, pp. 856–860 (1965)]. The enzymatic activity was expressed in terms of micromoles of p-nitrophenol isolated per minute on 1 mg of protein. The concentration of protein was measured in accordance with the method by Lowry et al. [J. Biol. Chem., 193, 265-273 (1951)].

Measurement of Deoxyribonucleic Acid (DNA) Content

A small fragment of the fempral diaphysis was subjected to homogenization for bone tissue, followed by its shaking together with 4.0 ml of 0.1N sodium hydroxide solution cooled with ice. After the thus-treated homogenate was subjected to alkali extraction, the extract was centrifuged at 10,000×g for 5 minutes. The thus-obtained supernatant liquid was used for the measurement in accordance with the Ceriotti method [J. Biol. Chem., 214, 39-77 (1955)]. The DNA content was expressed in terms of the total DNA content (mg) per gram of a wet bone.

Measurement of Zinc Content

A fragment of the femoral diaphysis was digested with nitric acid [Biochem. Pharmacol., 36, 4007-4012 (1986)] to measure the content of zinc by atomic adsorption spectrophotometry. The zinc content was expressed in terms of micrograms of zinc per gram of a wet bone. Results are shown in Table 1.

The data were shown as average value±standard error. The significant difference was determined using the Student's t-test. If the P value of a result was not greater than 0.05, the result was statistically regarded as being significantly different.

TABLE 1

|  | Calcium content (mg/g bone ash) | Alkaline phosphatase ($\mu$mol/min/mg protein) | DNA (mg/g wet bone) | Zinc ($\mu$g/g wet bone) |
| --- | --- | --- | --- | --- |
| Control | 386.5 ± 6.5 | 1599.6 ± 74.5 | 1.450 ± 0.020 | 156.9 ± 7.7 |
| L-carnosine zinc complex | 458.1 ± 8.7** | 1963.4 ± 118.3** | 2.931 ± 0.100** | 235.0 ± 9.1** |
| Zinc sulfate | 405.8 ± 4.5* | 2580.5 ± 80.3** | 1.510 ± 0.050 | 206.7 ± 9.8** |

*$p < 0.05$
**$p < 0.01$

As apparent from Table 1, zinc sulfate increased the zinc content, calcium content and alkaline phosphatase activity in the femoral diaphysis However, a significant change was not produced in the DNA content. On the other hand, the L-carnosine zinc complex increased the DNA content in addition to the zinc content, calcium content and alkaline phosphatase activity. As described above, it was confirmed that when L-carnosine zinc complex and zinc sulfate were separately dosed in the same amounts (5.5 mg/kg body weight) in terms of zinc, the L-carnosine zinc complex exerted stronger osteogenesis-stimulating action than zinc sulfate.

TEST EXAMPLE 2

Using Wister male and female rats of 150-200 g by weight regarding 10 rats as respective groups, the crystalline zinc complex of L-carnosine in a dose of 10 g/kg body weight) was orally administered to each rat. When observation was made for 7 days, dead cases were not recognized in both rat groups. On the other hand, it has been known that the $LD_{50}$ value for the oral administration of zinc sulfate is 1374 mg/kg [Safety Evaluation (II) for Chemical Substances, The Chemical Daily Co., Ltd., (1983)], and zinc sulfate is accompanied by side effects such as vomiting, nausea and diarrhea. Accordingly, it was confirmed that the L-carnosine zinc complex has safety higher than zinc sulfate.

EXAMPLE 1

| Crystalline L-carnosine zinc complex | 50 g |
| --- | --- |
| Lactose | 315 g |
| Corn starch | 125 g |
| Crystalline cellulose | 25 g |

The above components are mixed uniformly and added with 200 ml of a 7.5% aqueous solution of hydroxypropyl cellulose. The resultant mixture was formed into granules by an extrusion granulator making use of a screen 0.5 mm across. The thus-formed granules were immediately rounded by a "MARUMERIZER" and then dried, thereby providing a granular preparation.

EXAMPLE 2

| Crystalline L-carnosine zinc complex | 20 g |
| --- | --- |
| Lactose | 100 g |
| Corn starch | 36 g |
| Crystalline cellulose | 30 g |
| Calcium carboxymethyl cellulose | 10 g |
| Magnesium stearate | 4 g |

Components of the above composition were mixed uniformly to form tablets each having a weight of 200 mg by a single-punch tablet machine equipped with a pestle 7.5 mm across.

The thus-formed tablets were spray-coated with a coating solution having the following composition to give a coat weight of 10 mg, thereby providing an enteric-film-coated tablet preparation.

Composition of coating solution:

| Hydroxypropylmethyl cellulose phthalate | 8.0 (w/w) % |
| --- | --- |
| Glycerol fatty acid ester | 0.4 (w/w) % |
| Methylene chloride | 50.0 (w/w) % |
| Bleached beeswax | 0.1 (w/w) % |
| Isopropanol | 41.5 (w/w) % |

INDUSTRIAL APPLICABILITY

The osteogenesis promoters according to the present invention, which comprise, as an active ingredient, the zinc salt or complex of L-carnosine, are excellent in action to increase the calcium content, zinc content, DNA content and alkaline phosphatase activity in bones and extremely low in toxicity and side effects. These agents are therefore useful as medicines for treating fracture, osteomalacia, osteoporosis and low back pain, which are caused by a disorder of bone metabolism or osteogenesis. The present invention also features that the agents exhibit these effects by oral administration.

I claim:

1. An osteogenesis promoter comprising, as an active ingredient, a zinc salt or complex of L-carnosine.

2. The osteogenesis promoter according to claim 1, wherein said promoter further comprises a pharmaceutically acceptable adjuvant.

3. The osteogenesis promoter according to claim 2, wherein said promoter further comprises at least one member selected from the group consisting of excipients, binders, surfactants and lubricants.

4. The osteogenesis promoter according to claim 2, wherein said promoter further comprises a coating base selected from the group consisting of hydroxypropylmethyl cellulose phthalate, hydroxypropylmethyl cellulose acetate succinate, cellulose acetate phthalate and methacrylate copolymer.

5. The osteogenesis promoter according to claim 2, wherein said promoter further comprises a solvent selected from the group consisting of a medium-chain fatty acid triglyceride, safflower oil, soybean oil, polyethylene glycol 400, water, ethanol, and glycerol.

6. The osteogenesis promoter according to claim 3, wherein said promoter is a tablet, powder, granule or capsule suitable for oral administration; a solution suitable for parental injection; or a suppository.

7. The osteogenesis promoter according to claim 1, wherein said promoter contains of from 1-2000 mg of said active ingredient.

8. The osteogenesis promoter according to claim 7, wherein said promoter contains of from 10-200 mg of said active ingredient.

* * * * *